(12) United States Patent
Higuchi

(10) Patent No.: US 7,420,586 B2
(45) Date of Patent: Sep. 2, 2008

(54) ELECTRONIC ENDOSCOPE APPARATUS WHICH STORES IMAGE DATA ON RECORDING MEDIUM

(75) Inventor: Mitsuru Higuchi, Saitama (JP)

(73) Assignee: Fujinon Corporation, Saitama (JP)

( * ) Notice: Subject to any disclaimer, the term of this patent is extended or adjusted under 35 U.S.C. 154(b) by 855 days.

(21) Appl. No.: 10/973,895

(22) Filed: Oct. 27, 2004

(65) Prior Publication Data
US 2005/0093972 A1     May 5, 2005

(30) Foreign Application Priority Data
Oct. 29, 2003   (JP)   ............................. 2003-368276

(51) Int. Cl.
*H04N 7/18*   (2006.01)
(52) U.S. Cl. .......................................... 348/65; 348/61
(58) Field of Classification Search .................... 348/61, 348/65
See application file for complete search history.

(56) References Cited

U.S. PATENT DOCUMENTS
6,677,984 B2 *   1/2004   Kobayashi et al. ............ 348/65

FOREIGN PATENT DOCUMENTS
JP         2000-287203         10/2000

* cited by examiner

*Primary Examiner*—Allen Wong
(74) *Attorney, Agent, or Firm*—Birch, Stewart, Kolasch & Birch, LLP

(57) ABSTRACT

An electronic endoscope apparatus uses an image storage memory capable of storing image data of one or more examinations and records the image data on a recording medium. In response to a redisplay command, it judges whether the image size for a connected electronic scope matches the image size of the data in the image storage memory. If no match is found, the electronic endoscope apparatus changes the clock signal generated by a timing generator to the one suitable for the image size in the image storage memory and redisplays the image data read out of the image storage memory using the clock signal with this frequency on the monitor screen. This makes it possible to redisplay images of a finished examination easily in a constant screen display size.

3 Claims, 3 Drawing Sheets

ELECTRONIC ENDOSCOPE APPARATUS WHICH STORES IMAGE DATA ON RECORDING MEDIUM

BACKGROUND OF THE INVENTION

The application claims the priority of Japanese Patent Applications No. 2003-368276 filed on Oct. 29, 2003 which is incorporated herein by reference.

1. Field of the Invention

The present invention relates to an electronic endoscope apparatus. In particular, it relates to a configuration of an electronic endoscope apparatus which forms a digital image of an object under observation based on an output signal from a solid state image pickup device mounted on an electronic scope and can store image data of the digital image on a recording medium.

2. Description of the Related Art

Electronic endoscope apparatus have a solid state image pickup device such as a CCD (Charge Coupled Device) mounted on the tip of an electronic scope (electronic endoscope). The CCD images an object under observation illuminated by light from a light source. When imaging signals obtained by the CCD are outputted to a processor unit and subjected to various video processing in the processor unit, it becomes possible to display images of the object under observation on a monitor, record still images and the like on a recording device, and so on.

As also described in Japanese Patent Laid-Open No. 2000-287203, electronic endoscope apparatus of this type perform not only analog processing for output to a regular NTSC (PAL) monitor, but also digital image processing to output images of the object under observation for use on various external digital devices such as a personal computer monitor.

In view of the recent tendency toward higher pixel counts and higher resolution of CCDs which are solid state image pickup devices, it has been proposed to form digital images by making effective use of image information obtained by a CCD with a high pixel count. Specifically, there are standards such as VGA (Video Graphics Array) specification of 640 (horizontal)×480 (vertical) pixels, XGA (EXtended Graphics Array) specification of 1024×768 pixels, and SXGA (Super XGA) specification of 1280×960 pixels which differ in display pixel counts. Personal computers and the like can form image signals compliant with such a standard and use them on external digital devices and the like. Recording media for use on such external devices to record and store endoscope image data include PC cards, SmartMedia (registered trademark) cards, CompactFlash (registered trademark) cards, and MO (magneto-optical) disks.

However, since increases in the pixel count and resolution of a CCD increase the size of each image (data volume per image) obtained by the CCD, increasing the time required to transmit the image data, if it is necessary to wait for a recording process to complete each time image data is recorded on a recording medium, endoscopy cannot be conducted smoothly.

After a current examination, if images of the finished examination can be redisplayed easily on a monitor and the like before a next examination (of a next patient) is started, it will be useful in checking the results of the finished examination and providing an explanation to the patient, resulting in improved usability. However, if the electronic scope is replaced by another one equipped with a solid state image pickup device with a different pixel count for examination of the next patient after the examination, the clock frequency for image processing may change. In such a case, if images of the finished examination are displayed again, display size on the screen may change, resulting in hard-to-view images.

SUMMARY OF THE INVENTION

The present invention has been made in view of the above problems and has an object to provide an electronic endoscope apparatus which makes it possible to conduct endoscopy smoothly without waiting for completion of recording on a recording medium as well as to redisplay images of a finished examination easily in a constant screen display size.

To achieve the above object, the present invention provides an electronic endoscope apparatus, comprising: various electronic scopes each equipped with a solid state image pickup device with a different image size (pixel count); a processor unit which is removably connected with the electronic scopes and records, on a recording medium (information medium), image data of an object under observation formed based on output from the solid state image pickup device; a clock signal generator circuit which is mounted on the processor unit and generates clock signals with a plurality of frequencies according to image sizes obtained by the electronic scopes; an image storage memory which is mounted on the processor unit, stores image data in response to an image capture command, and transfers the image data to the recording medium; and a processor-side control circuit which judges in response to a redisplay command whether the image size (pixel count) for the connected electronic scope matches the image size (pixel count) of the data in the image storage memory, changes the clock signal generated by the clock signal generator circuit to the one suitable for the image size in the image storage memory if no match is found, and redisplays the image data read out of the image storage memory using the clock signal with this frequency on the display device.

The control circuit can erase the image data stored in the image storage memory, at the time of the first image capture during the next examination.

With the configuration of the present invention, if the operator gives a command to capture an image (still image) of an object under observation for the first time during endoscopy, the current image data is written into the image storage memory after clearing any image data of the previous examination in the image storage memory. Then, as the operator gives a record command, the image data within the image storage memory is transferred to and written into the recording medium. If the image storage memory has enough capacity to store image data for at least one examination (one patient), the endoscopy can be conducted smoothly without waiting for recording of each image to be completed.

If the operator gives a redisplay command after the examination, the appropriate image data is read out of the image storage memory, and thereby the image is redisplayed on a display device. In so doing, it is judged whether the image size for the connected electronic scope (solid state image pickup device) matches the image size in the image storage memory (the image sizes correspond to the pixel counts of images, and image processing clock frequencies may also be used for this judgment). If the image sizes do not match due to replacement of the electronic scope, the frequency of the clock signal is changed to the one suitable for the images in the image storage memory. This makes it possible to view endoscopic images in the same screen display size.

Furthermore the processor unit may comprise an examination start/stop switch which turns on and off the electronic scope separately from a processor main power switch; and a power supply control circuit which turns on and off power supply to the electronic scope through operation of the examination start/stop switch. Since the examination start/stop switch allows a scope power supply to be turned off independently, it is possible to remove the electronic scope while image data is being transferred from the image storage memory to the recording medium or redisplay images from the image storage memory with the electronic scope removed or with another electronic scope connected.

By using the image storage memory capable of storing image data of one or more examinations, the electronic endoscope apparatus according to the present invention makes it possible to conduct endoscopy smoothly without waiting for completion of recording on a recording medium as well as to redisplay images of a finished examination. Besides, by switching to a clock signal with a frequency suitable for the image size in the image storage memory, it is possible to redisplay images of the previous examination in the same image display size even if an electronic scope equipped with a solid state image pickup device with a different image size (pixel count) is connected for the next examination. This improves the usability of the apparatus.

DETAILED DESCRIPTION OF THE PREFERRED EMBODIMENTS

Figure 1:
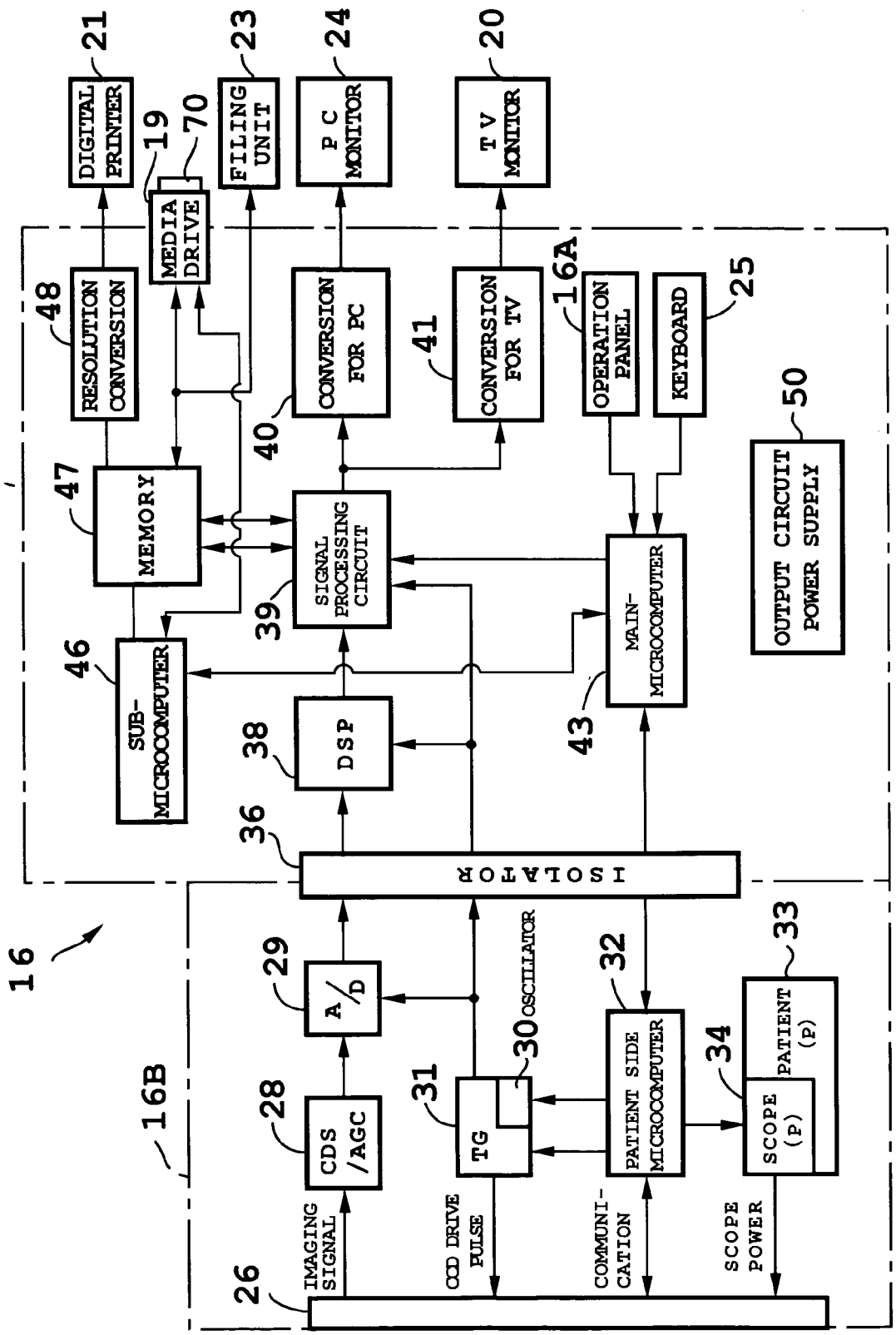
FIG. 1 is a circuit block diagram showing a configuration of an electronic endoscope apparatus (processor unit) according to an embodiment of the present invention.
Figure 2:
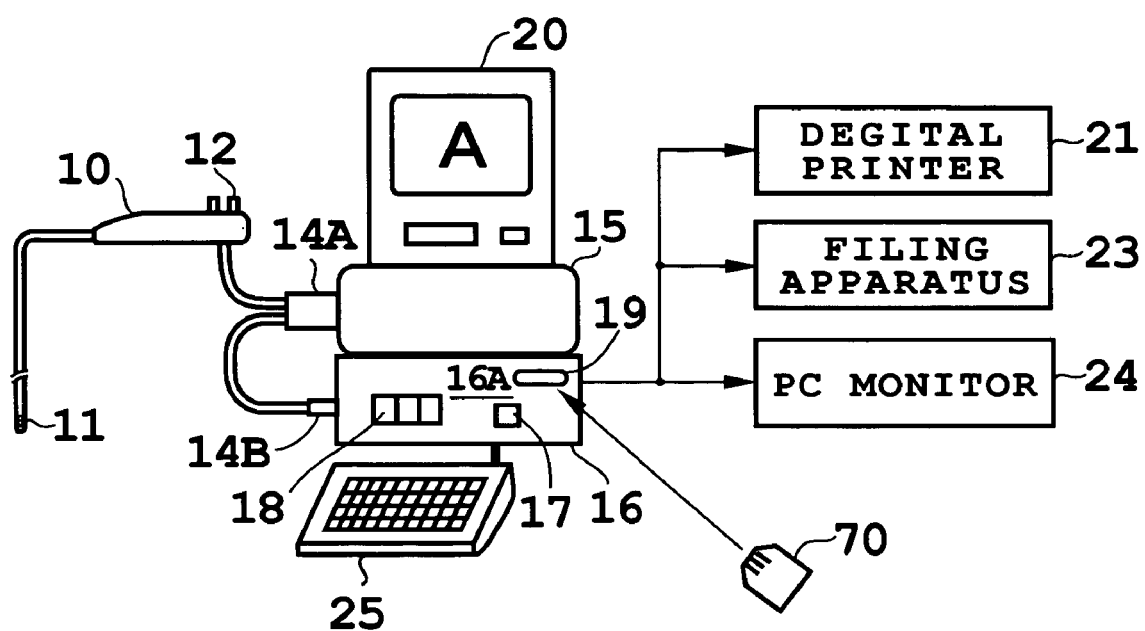
FIG. 2 is a diagram showing an overall configuration of the electronic endoscope apparatus according to the embodiment of the present invention.

FIGS. 1 and 2 show a configuration of an electronic endoscope apparatus according to an embodiment. First, an overall configuration will be described with reference to FIG. 2. As shown in FIG. 2, an electronic scope (electronic endoscope) 10 has a CCD 11 mounted on its tip. The CCD 11 is a solid state image pickup device and may be a 350,000-pixel CCD, 650,000-pixel CCD, or the like. Control switches including a freeze/record button 12 are mounted on a control panel of the electronic scope 10. The electronic scope 10 is connected with a light source 15 via a light guide connector 14A, and with a processor unit 16 via a signal/power line connector 14B. Light from the light source 15 is supplied to the tip through a light guide installed in the electronic scope 10 and an object under observation is imaged by the CCD 11 in the presence of an illuminating beam emitted from the tip.

On a front operation panel 16A of the processor unit 16, there are a main power switch (control button) 17 and examination start/stop switch (scope power-off switch) 18 as well as a loading slot of a media drive 19 located inside. The media drive 19 reads and writes data from/to recording media 70 such as a PC card or SmartMedia card. Also, as shown in FIG. 1, the processor unit 16 is connected with an NTSC (PAL) TV monitor 20, a digital printer 21, filing apparatus 23, personal computer (PC) monitor 24, keyboard 25, etc.

FIG. 1 shows a detailed internal configuration of the processor unit 16. The processor unit 16 is equipped with a patient circuit 16B which performs predetermined video processing and an output circuit 16C which forms signals in various output formats. A signal/power line connector 26 is connected with the signal/power line connector 14B from the electronic scope 10. The patient circuit 16B contains a CDS/AGC (Correlated Double Sampling/Automatic Gain Control) circuit 28 which samples and amplifies video signals from the CCD 11 and A/D converter 29.

Also, the processor unit 16 is equipped with an oscillator circuit 30 consisting of a plurality of quartz oscillators or LCR circuits as well as with a timing generator (TG) 31 which generates clock signals with a plurality of frequencies needed for processing of images of different image sizes and CCD drive pulses and the like to be supplied to the electronic scope 10. The timing generator 31 generates clock signals with frequencies of 14.313 MHz (for VGA image processing, for example), 20.00 MHz (for XGA image processing, for example), 24.54 MHz (for SXGA image processing, for example), etc. Furthermore, the processor unit 16 is equipped with a patient-side microcomputer 32 which acquires image size information (which may alternatively be pixel count information or reference clock frequency information) about the CCD 11 through communications with the electronic scope 10 and controls the patient circuit 16B. The patient-side microcomputer 32 determines the image size (or clock frequency) of the CCD 11 based on ID information or the like of the electronic scope 10.

Since this embodiment employs the examination start/stop switch 18 which turns off only the power supply to the electronic scope 10, thereby stopping the functions of the electronic scope 10, a patient power supply (P) 33 and scope power supply (P) 34 are provided. The scope power supply (P) 34 supplies power to the electronic scope 10 via the signal/power line connector 26 and its on/off operations are controlled by the patient-side microcomputer 32.

The patient circuit 16B is connected with the output circuit 16C via an isolator (electrical isolation means) 36. The output circuit 16C is equipped with a DSP (Digital Signal Processor) 38 and signal processing circuit 39 which perform various image processing on digital video signals, a PC resolution converter circuit 40 which converts output of signal processing circuit 39 into a predetermined resolution (e.g., image size compliant with VGA, XGA, or the like) for display on the PC monitor 24, a TV resolution converter circuit 41 which converts the output into an analog signal (Y/C signal or the like) of a resolution (image size) for display on the NTSC (PAL) TV monitor 20.

The output circuit 16C is also equipped with a main microcomputer 43 which totally controls the circuits in the processor unit 16; the sub-microcomputer 46 which controls image data writes and reads into/from a memory 47 described later and controls the media drive 19; and the image storage memory 47 connected to the media drive 19 and capable of storing at least one set of examination data (e.g., approximately 100 images) to transfer examination images to the recording medium 70. If a redisplay key on the keyboard 25 is pressed before the image data in the image storage memory 47 is erased, the main microcomputer 43 compares image size information between the data in the image storage memory 47 and the currently connected electronic scope 10, i.e., it compares the image size information received from the sub-microcomputer 46 with the image size information received from the patient-side microcomputer 32, to see if the two image sizes (or reference clock frequencies) match. If they do not match, the main microcomputer 43 controls that a clock frequency suitable for the images in the image storage memory 47 is selected.

Furthermore, the image storagememory 47 is equipped with a resolution converter circuit 48 which forms digital image signals compliant with, for example, the VGA, XGA, SXGA, or other standard to output them to the digital printer 21. Incidentally, an output circuit power supply (P) 50 is installed in the output circuit 16C.

So much for the configuration of the embodiment. To begin with, when the operator presses the main power switch 17 on the operation panel 16A, power is supplied from the power supplies 50, 33, and 34 to the appropriate circuits and the CCD 11 at the tip of the electronic scope 10 starts imaging. The signal outputted from the CCD 11 goes through various digital video processing in the CDS/AGC circuit 28, A/D converter 29, DSP 38, and signal processing circuit 39. Then, the video signal is supplied to the PC monitor 24 via the PC resolution converter circuit 40 and to the TV monitor 20 via the TV resolution converter circuit 41, and consequently, video images of the object under observation are displayed on the monitors.

If the operator presses the first stage of the freeze/record button 12, thereby giving the first image capture command, still images stored in frame memories or the like in the resolution converter circuits 40 and 41 are displayed on the TV monitor 20 and PC monitor 24, respectively. At the same time, image data of the previous examination in the image storage memory 47 is cleared and image data of the first image of the current examination is written into the image storage memory 47. Then, if the operator presses the second stage of the freeze/record button 12 by looking at the TV monitor 20 or the like, the image data stored in the image storage memory 47 is transferred to and recorded on the recording medium 70.

As described above, by using the image storage memory 47 capable of storing image data of one or more examinations, the above embodiment allows endoscopy to be conducted smoothly without being obstructed by operations of a recording process with respect to the recording medium 70. However, there can be a situation where recording operations with respect to the recording medium 70 and the like are not completed even after endoscopy is finished. Thus, in order for a recording operation to be carried out until it is completed, this embodiment uses the examination start/stop switch 18 which turns off (shuts down) only the scope power supply 34 without turning off the patient power supply 33 or output circuit power supply 50. This makes it possible to quickly carry out subsequent operations including cleaning and disinfection of the electronic scope 10 after an examination, connection of the another electronic scope for the next examination, etc.

Figure 3:
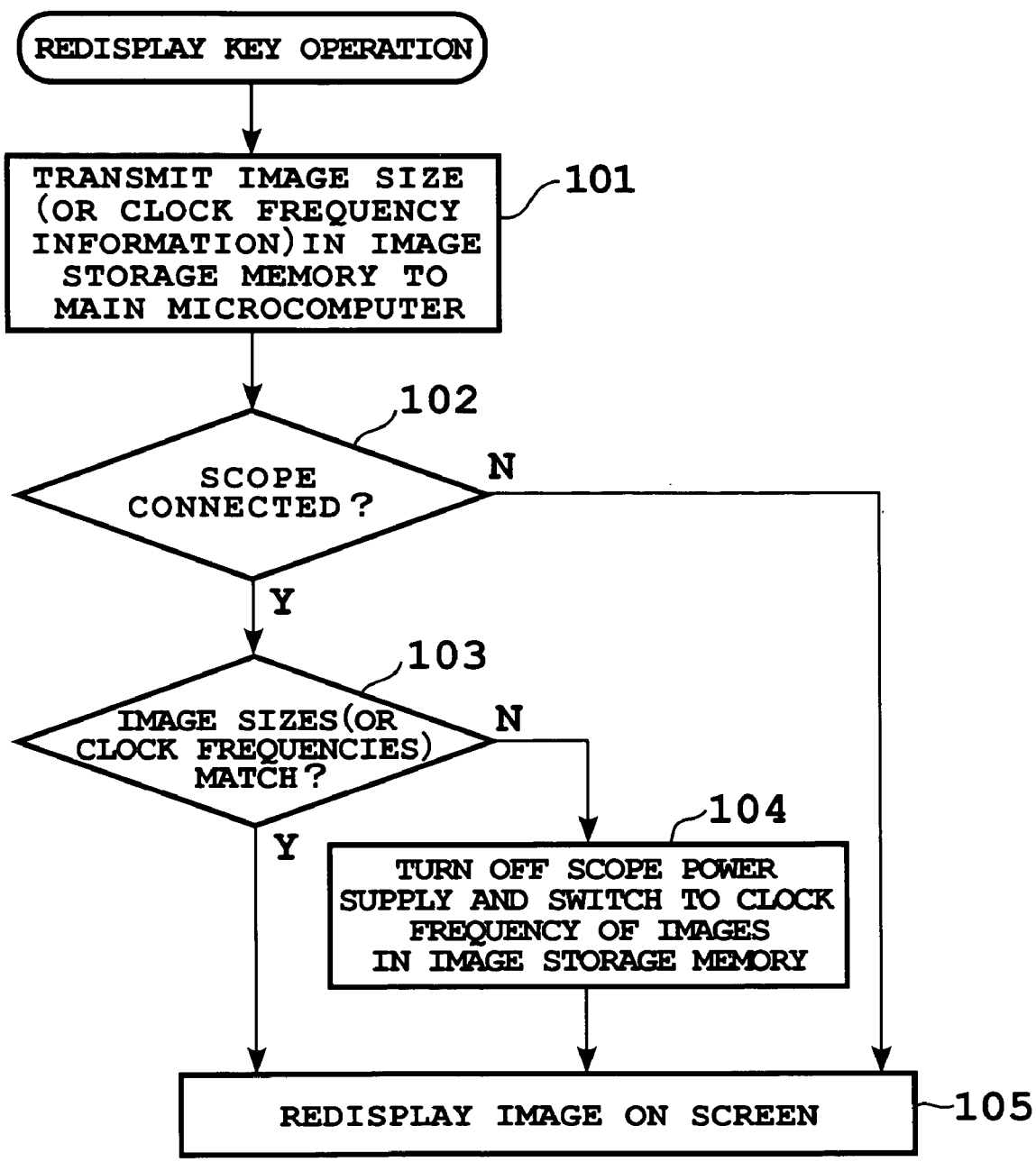
FIG. 3 is a flowchart diagram showing operation of the embodiment.

FIG. 3 shows image redisplay operation. According to this embodiment, image data in the image storage memory 47 is retained until the first image capture in the next examination, making it possible to redisplay images of the previous examination. Specifically, if the redisplay key on the keyboard 25 is pressed before the first image capture in the next examination as shown in FIG. 3, image size information (which is pixel count information, but may alternatively be clock frequency information) about the data in the image storage memory 47 is transmitted from the sub-microcomputer 46 which stores the information to the main microcomputer 43 (Step 101). Next, in Step 102, the processor unit 16 judges whether an electronic scope 10 is connected. If the answer is N (NO), the processor unit 16 goes to Step 105, where it reads data from the image storage memory 47 based on the clock signal with the current frequency, thereby redisplays the selected image of the previous examination.

On the other hand, if the answer in Step 102 is Y (YES), the processor unit 16 judges in Step 103 whether the image size (or corresponding clock frequency) for the current electronic scope 10 (the CCD 11) matches the image size (or corresponding clock frequency) of the data in the image storage memory 47. If the answer is Y, the processor unit 16 similarly reads data from the image storage memory 47 based on the clock signal with the current frequency in Step 105, thereby redisplays the image of the previous examination.

If the answer in Step 103 is N, the processor unit 16 goes to Step 104, where it turns off the scope power supply 34 and switches to the clock frequency suitable for the image size of the data in the image storage memory 47. Then, is goes to Step 105. For example, if the images of the previous examination is based on a 20.00-MHz clock signal while the images acquired by the connected electronic scope 10 is based on a 24.54-MHz clock signal, a 20.00-MHz clock signal is formed instead of the 24.54-MHz clock signal generated by the timing generator 31 and image data is read out of the image storage memory 47 based on the 20.00-MHz clock signal, and consequently, an image of the object under observation is displayed on the monitor 20 screen. In this way, the screen display size of the redisplay image coincides with the display size used in the previous examination, making it possible to view images of the object under observation always in the same screen display size.

Although in the above embodiment, image data is captured into the image storage memory 47 when the freeze switch (first stage of the freeze/record button 12) is pressed, it is also possible to capture the image data into the image storage memory 47 when the record switch (second stage of the freeze/record button 12) is pressed.

What is claimed is:

1. An electronic endoscope apparatus, comprising:
   various electronic scopes each equipped with a solid state image pickup device with a different image size;
   a processor unit which is removably connected with the electronic scopes and records, on a recording medium, image data of an object under observation formed based on output from the solid state image pickup device;
   a clock signal generator circuit which is mounted on the processor unit and generates clock signals with a plurality of frequencies according to image sizes obtained by the electronic scopes;
   an image storage memory which is mounted on the processor unit, stores image data in response to an image capture command, and transfers the image data to the recording medium; and
   a processor-side control circuit which judges in response to a redisplay command whether the image size for the connected electronic scope matches the image size of the data in the image storage memory, changes the clock signal generated by the clock signal generator circuit to the one suitable for the image size in the image storage memory if no match is found, and redisplays the image data read out of the image storage memory using the clock signal with this frequency on the display device.

2. The electronic endoscope apparatus according to claim 1, wherein the control circuit erases the image data stored in the image storage memory, at the time of the first image capture during the next examination.

3. The electronic endoscope apparatus according to claim 1, wherein the processor unit comprises an examination start/stop switch which turns on and off the electronic scope separately from a processor main power switch; and a power supply control circuit which turns on and off power supply to the electronic scope through operation of the examination start/stop switch.

* * * * *